(12) United States Patent
Yokoyama et al.

(10) Patent No.: US 6,723,543 B1
(45) Date of Patent: Apr. 20, 2004

(54) MUTANT KANAMYCIN NUCLEOTIDYLTRANSFERASES FROM S. AUREUS

(75) Inventors: Sigeyuki Yokoyama, Saitama (JP); Jun Hoseki, Hyogo (JP); Takato Yano, Osaka (JP); Yoshinori Koyama, Ibaraki (JP); Seiki Kuramitsu, Osaka (JP); Hiroyuki Kagamiyama, Hyogo (JP)

(73) Assignee: Riken, Saitama (JP)

( * ) Notice: Subject to any disclaimer, the term of this patent is extended or adjusted under 35 U.S.C. 154(b) by 65 days.

(21) Appl. No.: 09/697,186

(22) Filed: Oct. 27, 2000

(30) Foreign Application Priority Data

Oct. 29, 1999 (JP) .............................. 11-309616

(51) Int. Cl.[7] .............................. C12N 9/10
(52) U.S. Cl. ...................................... 435/193
(58) Field of Search ............................ 435/194

(56) References Cited

PUBLICATIONS

Matsumura et al. Single amino acid replacements affecting the thermostability of kanamycin nucleotidyltransferase. Molecular General Genetics (MGG) 1986 204:355–358.*

Jun Hoseki, et al. "Directed Evolution of Thermostable Kanamycin–Resistance Gene: A Convenient Selection Marker for *Thermus thermophilus*" *J. Biochem.* 126(5):951–956 (1999).

Masazumi Matsumura et al. "Screening for Thermostable Mutant of Kanamycin Nucleotidyltransferase by the Use of a Transformation System for a Thermophile, *Bacillus stearothermophilus*" *J. Biol. Chem.* 260(28):15298–15303 (1985).

Hans H. Liao "Thermostable Mutants of Kanamycin Nucleotidyltransferase are also More Stable to Proteinase K, Urea, Detergents, and Water–Miscible Organic Solvents" *Enzyme Microb. Technol.* 15(4):286–292 (1993).

* cited by examiner

*Primary Examiner*—Ponnathapura Achutamurthy
*Assistant Examiner*—Kathleen Kerr
(74) *Attorney, Agent, or Firm*—Finnegan, Henderson, Farabow, Garrett & Dunner LLP

(57) ABSTRACT

It is desirable to have selective markers suitable for screening of thermophilic bacteria such as *Thermus thermophilus*. *T. thermophilus* are good research materials for investigating the interrelation between enzyme structures and functions since they are stable at extreme pH, crystallize easily and are easy-to-handle. Novel mutants of *Staphylococcus aureus* kanamydn nucleotidyltransferase with markedly improved thermostability are disclosed, as well as a selective marker using the same, and a screening method for thermophilic bacteria such as *T. thermophilus* using said selective marker.

12 Claims, 5 Drawing Sheets

SEQUENCE LISTING

```
<160> NUMBER OF SEQ ID NOS: 20

<210> SEQ ID NO 1
<211> LENGTH: 253
<212> TYPE: PRT
<213> ORGANISM: Artificial Sequence
<220> FEATURE:
<223> OTHER INFORMATION: Description of Artificial Sequence: Mutant
      enzyme obtained by introduction of point mutation into
      wild type KNT gene of Staphylococcus aureus and
      its expression

<400> SEQUENCE: 1

Met Asn Gly Pro Ile Ile Met Thr Arg Glu Glu Arg Met Lys Ile Val
 1               5                  10                  15

His Glu Ile Lys Glu Arg Ile Leu Asp Lys Tyr Gly Asp Asp Val Lys
            20                  25                  30

Ala Ile Gly Val Tyr Gly Ser Leu Gly Arg Gln Thr Asp Gly Pro Tyr
        35                  40                  45

Ser Asp Ile Glu Met Met Cys Val Met Ser Thr Glu Glu Ala Glu Phe
    50                  55                  60

Ser His Glu Trp Thr Thr Gly Glu Trp Lys Val Glu Val Asn Phe Tyr
65                  70                  75                  80

Ser Glu Glu Ile Leu Leu Asp Tyr Ala Ser Gln Val Glu Ser Asp Trp
                85                  90                  95

Pro Leu Thr His Gly Gln Phe Phe Ser Ile Leu Pro Ile Tyr Asp Ser
            100                 105                 110

Gly Gly Tyr Leu Glu Lys Val Tyr Gln Thr Ala Lys Ser Val Glu Ala
        115                 120                 125

Gln Lys Phe His Asp Ala Ile Cys Ala Leu Ile Val Glu Glu Leu Phe
    130                 135                 140

Glu Tyr Ala Gly Lys Trp Arg Asn Ile Arg Val Gln Gly Pro Thr Thr
145                 150                 155                 160

Phe Leu Pro Ser Leu Thr Val Gln Val Ala Met Ala Gly Ala Met Leu
                165                 170                 175

Ile Gly Leu His His Arg Ile Cys Tyr Thr Thr Ser Ala Ser Val Leu
            180                 185                 190

Thr Glu Ala Val Lys Gln Ser Asp Leu Pro Ser Gly Tyr Asp His Leu
        195                 200                 205

Cys Gln Phe Val Met Ser Gly Gln Leu Ser Asp Ser Glu Lys Leu Leu
    210                 215                 220

Glu Ser Leu Glu Asn Phe Trp Asn Gly Ile Gln Glu Trp Thr Glu Arg
225                 230                 235                 240

His Gly Tyr Ile Val Asp Val Ser Lys Arg Ile Pro Phe
                245                 250

<210> SEQ ID NO 2
<211> LENGTH: 253
<212> TYPE: PRT
<213> ORGANISM: Artificial Sequence
<220> FEATURE:
<223> OTHER INFORMATION: Description of Artificial Sequence: Mutant
      enzyme obtained by introduction of point mutation into
``` wild type KNT gene of Staphylococcus aureus and
        its expression

<400> SEQUENCE: 2

Met Lys Gly Pro Ile Ile Met Thr Arg Glu Glu Arg Met Lys Ile Val
 1               5                  10                  15

His Glu Ile Lys Glu Arg Ile Leu Asp Lys Tyr Gly Asp Asp Val Lys
             20                  25                  30

Ala Ile Gly Val Tyr Gly Ser Leu Gly Arg Gln Thr Asp Gly Pro Tyr
         35                  40                  45

Ser Asp Ile Glu Met Met Cys Val Met Ser Thr Glu Gly Ala Glu Phe
 50                  55                  60

Ser Tyr Glu Trp Thr Thr Gly Glu Trp Lys Ala Glu Val Asn Phe Tyr
 65                  70                  75                  80

Ser Glu Glu Ile Leu Leu Asp Tyr Ala Ser Arg Val Glu Ser Asp Trp
                 85                  90                  95

Pro Leu Thr His Gly Arg Phe Phe Ser Ile Leu Pro Ile Tyr Asp Pro
             100                 105                 110

Gly Gly Tyr Phe Glu Lys Val Tyr Gln Thr Ala Lys Ser Val Glu Ala
         115                 120                 125

Gln Lys Phe His Asp Ala Ile Cys Ala Leu Ile Val Glu Glu Leu Phe
130                 135                 140

Glu Tyr Ala Gly Lys Trp Arg Asn Ile Arg Val Gln Gly Pro Thr Thr
145                 150                 155                 160

Phe Leu Pro Ser Leu Thr Val Gln Val Ala Met Ala Gly Ala Met Leu
                165                 170                 175

Ile Gly Leu His His Arg Ile Cys Tyr Thr Thr Ser Ala Ser Val Leu
            180                 185                 190

Thr Glu Ala Val Lys Gln Pro Asp Leu Pro Ser Gly Tyr Asp His Leu
        195                 200                 205

Cys Gln Leu Val Met Ser Gly Gln Leu Ser Asp Ser Glu Lys Leu Leu
    210                 215                 220

Glu Ser Leu Glu Asn Phe Trp Asn Gly Ile Gln Glu Trp Thr Glu Arg
225                 230                 235                 240

His Gly Tyr Ile Val Asp Val Ser Lys Arg Ile Pro Phe
                245                 250

<210> SEQ ID NO 3
<211> LENGTH: 253
<212> TYPE: PRT
<213> ORGANISM: Artificial Sequence
<220> FEATURE:
<223> OTHER INFORMATION: Description of Artificial Sequence: Mutant
      enzyme obtained by introduction of point mutation into
      wild type KNT gene of Staphylococcus aureus and
      its expression

<400> SEQUENCE: 3

Met Lys Gly Pro Ile Ile Met Thr Arg Glu Glu Arg Met Lys Ile Val
 1               5                  10                  15

His Glu Ile Lys Glu Arg Ile Leu Asp Lys Tyr Gly Asp Asp Val Lys
             20                  25                  30

Ala Ile Gly Val Tyr Gly Ser Leu Gly Arg Gln Thr Asp Gly Pro Tyr
         35                  40                  45

Ser Asp Ile Glu Met Met Cys Val Leu Ser Thr Glu Gly Val Glu Phe
 50                  55                  60

Ser Tyr Glu Trp Thr Thr Gly Glu Trp Lys Ala Glu Val Asn Phe Tyr

-continued

```
                65                  70                  75                  80
Ser Glu Glu Ile Leu Leu Asp Tyr Ala Ser Arg Val Glu Pro Asp Trp
                        85                  90                  95

Pro Leu Thr His Gly Arg Phe Phe Ser Ile Leu Pro Ile Tyr Asp Pro
            100                 105                 110

Gly Gly Tyr Phe Glu Lys Val Tyr Gln Thr Ala Lys Ser Val Glu Ala
        115                 120                 125

Gln Lys Phe His Asp Ala Ile Cys Ala Leu Ile Val Glu Glu Leu Phe
    130                 135                 140

Glu Tyr Ala Gly Lys Trp Arg Asn Ile Arg Val Gln Gly Pro Thr Thr
145                 150                 155                 160

Phe Leu Pro Ser Leu Thr Val Gln Val Ala Met Ala Gly Ala Met Leu
                165                 170                 175

Ile Gly Leu His His Arg Ile Cys Tyr Thr Thr Ser Ala Ser Val Leu
            180                 185                 190

Thr Glu Ala Val Lys Gln Pro Asp Leu Pro Pro Gly Tyr Val Gln Leu
        195                 200                 205

Cys Gln Leu Val Met Ser Gly Gln Leu Ser Asp Pro Glu Lys Leu Leu
    210                 215                 220

Glu Ser Leu Glu Asn Phe Trp Asn Gly Val Gln Glu Trp Ala Glu Arg
225                 230                 235                 240

His Gly Tyr Ile Val Asp Val Ser Lys Arg Ile Pro Phe
                245                 250

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 4
gactgtacgg gtacccgttg acggcggata tggta                              35

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 5
gactgtacgc tgcagcgtaa ccaacatgat taaca                              35

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Primer for
      PCR amplification

<400> SEQUENCE: 6
gactgtacgg aattcgagct cgagcaaatc taaaa                              35

<210> SEQ ID NO 7
<211> LENGTH: 35
<212> TYPE: DNA
<213> ORGANISM: Artificial Sequence
```

-continued

```
<220> FEATURE:
<223> OTHER INFORMATION: Description of Artificial Sequence: Primer for
      subcloning of WT

<400> SEQUENCE: 7
gactgtacgc atatgaatgg accaataata atgac                               35

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Primer for
      subcloning of KT3-11 and HTK

<400> SEQUENCE: 8
gactgtacgc atatgaaagg accaataata atgac                               35

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Primer for
      subcloning

<400> SEQUENCE: 9
gactgtacgc tcgagcgtaa ccaacatgat taaca                               35

<210> SEQ ID NO 10
<211> LENGTH: 759
<212> TYPE: DNA
<213> ORGANISM: Staphylococcus aureus
<220> FEATURE:
<221> NAME/KEY: CDS
<222> LOCATION: (1)..(759)

<400> SEQUENCE: 10 gtg aat gga cca ata ata atg act aga gaa gaa aga atg aag att gtt     48
Met Asn Gly Pro Ile Ile Met Thr Arg Glu Glu Arg Met Lys Ile Val
 1               5                  10                  15 cat gaa att aag gaa cga ata ttg gat aaa tat ggg gat gat gtt aag     96
His Glu Ile Lys Glu Arg Ile Leu Asp Lys Tyr Gly Asp Asp Val Lys
             20                  25                  30 gct att ggt gtt tat ggc tct ctt ggt cgt cag act gat ggg ccc tat    144
Ala Ile Gly Val Tyr Gly Ser Leu Gly Arg Gln Thr Asp Gly Pro Tyr
         35                  40                  45 tcg gat att gag atg atg tgt gtc atg tca aca gag gaa gca gag ttc    192
Ser Asp Ile Glu Met Met Cys Val Met Ser Thr Glu Glu Ala Glu Phe
     50                  55                  60 agc cat gaa tgg aca acc ggt gag tgg aag gtg gaa gtg aat ttt gat    240
Ser His Glu Trp Thr Thr Gly Glu Trp Lys Val Glu Val Asn Phe Asp
 65                  70                  75                  80 agc gaa gag att cta cta gat tat gca tct cag gtg gaa tca gat tgg    288
Ser Glu Glu Ile Leu Leu Asp Tyr Ala Ser Gln Val Glu Ser Asp Trp
                 85                  90                  95 ccg ctt aca cat ggt caa ttt ttc tct att ttg ccg att tat gat tca    336
Pro Leu Thr His Gly Gln Phe Phe Ser Ile Leu Pro Ile Tyr Asp Ser
            100                 105                 110 ggt gga tac tta gag aaa gtg tat caa act gct aaa tcg gta gaa gcc    384
Gly Gly Tyr Leu Glu Lys Val Tyr Gln Thr Ala Lys Ser Val Glu Ala
        115                 120                 125 caa acg ttc cac gat gcg att tgt gcc ctt atc gta gaa gag ctg ttt    432
Gln Thr Phe His Asp Ala Ile Cys Ala Leu Ile Val Glu Glu Leu Phe
```

|  |  |
|---|---|
| gaa tat gca ggc aaa tgg cgt aat att cgt gtg caa gga ccg aca aca<br>Glu Tyr Ala Gly Lys Trp Arg Asn Ile Arg Val Gln Gly Pro Thr Thr<br>145                    150                    155                    160 | 480 |
| ttt cta cca tcc ttg act gta cag gta gca atg gca ggt gcc atg ttg<br>Phe Leu Pro Ser Leu Thr Val Gln Val Ala Met Ala Gly Ala Met Leu<br>                    165                    170                    175 | 528 |
| att ggt ctg cat cat cgc atc tgt tat acg acg agc gct tcg gtc tta<br>Ile Gly Leu His His Arg Ile Cys Tyr Thr Thr Ser Ala Ser Val Leu<br>                  180                    185                    190 | 576 |
| act gaa gca gtt aag caa tca gat ctt cct tca ggt tat gac cat ctg<br>Thr Glu Ala Val Lys Gln Ser Asp Leu Pro Ser Gly Tyr Asp His Leu<br>          195                    200                    205 | 624 |
| tgc cag ttc gta atg tct ggt caa ctt tcc gac tct gag aaa ctt ctg<br>Cys Gln Phe Val Met Ser Gly Gln Leu Ser Asp Ser Glu Lys Leu Leu<br>210                    215                    220 | 672 |
| gaa tcg cta gag aat ttc tgg aat ggg att cag gag tgg aca gaa cga<br>Glu Ser Leu Glu Asn Phe Trp Asn Gly Ile Gln Glu Trp Thr Glu Arg<br>225                    230                    235                    240 | 720 |
| cac gga tat ata gtg gat gtg tca aaa cgc ata cca ttt<br>His Gly Tyr Ile Val Asp Val Ser Lys Arg Ile Pro Phe<br>                  245                    250 | 759 |

<210> SEQ ID NO 11
<211> LENGTH: 253
<212> TYPE: PRT
<213> ORGANISM: Staphylococcus aureus

<400> SEQUENCE: 11

Met Asn Gly Pro Ile Ile Met Thr Arg Glu Glu Arg Met Lys Ile Val
 1               5                  10                  15

His Glu Ile Lys Glu Arg Ile Leu Asp Lys Tyr Gly Asp Val Lys
             20                  25                  30

Ala Ile Gly Val Tyr Gly Ser Leu Gly Arg Gln Thr Asp Gly Pro Tyr
         35                  40                  45

Ser Asp Ile Glu Met Met Cys Val Met Ser Thr Glu Glu Ala Glu Phe
     50                  55                  60

Ser His Glu Trp Thr Thr Gly Glu Trp Lys Val Glu Val Asn Phe Asp
 65                  70                  75                  80

Ser Glu Glu Ile Leu Leu Asp Tyr Ala Ser Gln Val Glu Ser Asp Trp
                 85                  90                  95

Pro Leu Thr His Gly Gln Phe Phe Ser Ile Leu Pro Ile Tyr Asp Ser
            100                 105                 110

Gly Gly Tyr Leu Glu Lys Val Tyr Gln Thr Ala Lys Ser Val Glu Ala
        115                 120                 125

Gln Thr Phe His Asp Ala Ile Cys Ala Leu Ile Val Glu Glu Leu Phe
    130                 135                 140

Glu Tyr Ala Gly Lys Trp Arg Asn Ile Arg Val Gln Gly Pro Thr Thr
145                 150                 155                 160

Phe Leu Pro Ser Leu Thr Val Gln Val Ala Met Ala Gly Ala Met Leu
                165                 170                 175

Ile Gly Leu His His Arg Ile Cys Tyr Thr Thr Ser Ala Ser Val Leu
            180                 185                 190

Thr Glu Ala Val Lys Gln Ser Asp Leu Pro Ser Gly Tyr Asp His Leu
        195                 200                 205

Cys Gln Phe Val Met Ser Gly Gln Leu Ser Asp Ser Glu Lys Leu Leu
    210                 215                 220

Glu Ser Leu Glu Asn Phe Trp Asn Gly Ile Gln Glu Trp Thr Glu Arg
225                 230                 235                 240

His Gly Tyr Ile Val Asp Val Ser Lys Arg Ile Pro Phe
                245                 250

<210> SEQ ID NO 12
<211> LENGTH: 253
<212> TYPE: PRT
<213> ORGANISM: Artificial Sequence
<220> FEATURE:
<223> OTHER INFORMATION: Description of Artificial Sequence: Mutant
      enzyme obtained by introduction of point mutation into
      wild type KNT gene of Staphylococcus aureus and
      its expression

<400> SEQUENCE: 12

Met Asn Gly Pro Ile Ile Met Thr Arg Glu Glu Arg Met Lys Ile Val
1               5                   10                  15

Tyr Glu Ile Lys Glu Arg Ile Leu Asp Lys Tyr Gly Asp Asp Val Lys
                20                  25                  30

Ala Ile Gly Val Tyr Gly Ser Leu Gly Arg Gln Thr Asp Gly Pro Tyr
            35                  40                  45

Ser Asp Ile Glu Met Met Cys Val Met Ser Thr Glu Glu Ala Glu Phe
    50                  55                  60

Ser His Glu Trp Thr Thr Gly Glu Trp Lys Ala Glu Val Asn Phe Tyr
65                  70                  75                  80

Ser Glu Glu Ile Leu Leu Asp Tyr Ala Ser Arg Val Glu Ser Asp Trp
                85                  90                  95

Pro Leu Thr His Gly Arg Phe Phe Ser Ile Leu Pro Ile Tyr Asp Pro
            100                 105                 110

Gly Gly Tyr Phe Glu Lys Val Tyr Gln Thr Ala Lys Ser Val Glu Ala
        115                 120                 125

Gln Lys Phe His Asp Ala Ile Cys Ala Leu Ile Val Glu Glu Leu Phe
    130                 135                 140

Glu Tyr Ala Gly Lys Trp Arg Asn Ile Arg Val Gln Gly Pro Thr Thr
145                 150                 155                 160

Phe Leu Pro Ser Leu Thr Val Gln Val Ala Met Ala Gly Ala Met Leu
                165                 170                 175

Ile Gly Leu His His Arg Ile Cys Tyr Thr Thr Ser Ala Ser Val Leu
            180                 185                 190

Thr Glu Ala Leu Lys Gln Ser Asp Leu Pro Ser Gly Tyr Asp His Leu
        195                 200                 205

Cys Gln Phe Val Met Ser Gly Gln Leu Ser Asp Ser Glu Lys Leu Leu
    210                 215                 220

Glu Ser Leu Glu Asn Phe Trp Asn Gly Val Gln Glu Trp Ala Glu Arg
225                 230                 235                 240

His Gly Tyr Ile Val Asp Val Ser Lys Arg Ile Pro Phe
                245                 250

<210> SEQ ID NO 13
<211> LENGTH: 253
<212> TYPE: PRT
<213> ORGANISM: Artificial Sequence
<220> FEATURE:
<223> OTHER INFORMATION: Description of Artificial Sequence: Mutant
      enzyme obtained by introduction of point mutation into
      wild type KNT gene of Staphylococcus aureus and
      its expression

```
<400> SEQUENCE: 13

Met Asn Gly Pro Ile Ile Met Thr Arg Glu Glu Arg Met Lys Ile Val
  1               5                  10                  15

His Glu Ile Lys Glu Arg Ile Leu Asn Lys Tyr Gly Asp Asp Val Lys
                 20                  25                  30

Ala Ile Gly Val Tyr Gly Ser Leu Gly Arg Gln Thr Asp Gly Pro Tyr
             35                  40                  45

Ser Asp Ile Glu Met Met Cys Val Leu Ser Thr Glu Gly Val Glu Phe
 50                  55                  60

Ser His Glu Trp Thr Thr Gly Glu Trp Lys Ala Glu Val Asn Phe Tyr
 65                  70                  75                  80

Ser Glu Glu Ile Leu Leu Asp Tyr Ala Ser Gln Val Glu Pro Asp Trp
                 85                  90                  95

Pro Leu Thr His Gly Arg Phe Phe Ser Ile Leu Pro Ile Tyr Asp Ser
                100                 105                 110

Gly Gly Tyr Leu Gly Lys Val Tyr Gln Thr Ala Lys Ser Val Glu Ala
            115                 120                 125

Gln Lys Phe His Asp Ala Ile Cys Ala Leu Ile Val Glu Glu Leu Phe
130                 135                 140

Glu Tyr Ala Gly Lys Trp Arg Asn Ile Arg Val Gln Gly Pro Thr Thr
145                 150                 155                 160

Phe Leu Pro Ser Leu Thr Val Gln Val Ala Met Ala Gly Ala Met Leu
                165                 170                 175

Ile Gly Leu His His Arg Ile Cys Tyr Thr Thr Ser Ala Leu Val Leu
                180                 185                 190

Thr Glu Ala Val Lys Gln Ser Asp Leu Pro Ser Gly Tyr Asp His Leu
            195                 200                 205

Cys Gln Leu Val Met Ser Gly Gln Leu Ser Asp Ser Glu Lys Leu Leu
210                 215                 220

Glu Ser Leu Glu Asn Phe Trp Asn Gly Ile Gln Glu Trp Thr Glu Arg
225                 230                 235                 240

His Gly Tyr Ile Val Asp Val Ser Lys Arg Ile Pro Phe
                245                 250

<210> SEQ ID NO 14
<211> LENGTH: 253
<212> TYPE: PRT
<213> ORGANISM: Artificial Sequence
<220> FEATURE:
<223> OTHER INFORMATION: Description of Artificial Sequence: Mutant
      enzyme obtained by introduction of point mutation into
      wild type KNT gene of Staphylococcus aureus and
      its expression

<400> SEQUENCE: 14

Met Asn Gly Pro Ile Ile Met Thr Arg Glu Glu Arg Met Lys Ile Val
  1               5                  10                  15

His Glu Ile Lys Glu Arg Ile Leu Asp Lys Tyr Gly Asp Asp Val Lys
                 20                  25                  30

Ala Ile Gly Val Tyr Gly Ser Leu Gly Arg Gln Thr Asp Gly Pro Tyr
             35                  40                  45

Ser Asp Ile Glu Met Met Cys Val Met Ser Thr Glu Gly Ala Glu Phe
 50                  55                  60

Ser Tyr Glu Trp Thr Thr Gly Glu Trp Lys Ala Glu Val Asn Phe Tyr
 65                  70                  75                  80

Ser Glu Glu Ile Leu Leu Asp Tyr Ala Ser Arg Val Glu Pro Asp Trp
```

```
                        85                  90                  95
Pro Leu Thr His Gly Arg Phe Phe Ser Ile Leu Pro Ile Tyr Asp Ser
                100                 105                 110

Gly Gly Tyr Leu Glu Lys Val Tyr Gln Thr Ala Lys Ser Val Glu Ala
            115                 120                 125

Gln Lys Phe His Asp Ala Ile Cys Ala Leu Ile Val Glu Glu Leu Phe
        130                 135                 140

Glu Tyr Ala Gly Lys Trp Arg Asn Ile Arg Val Gln Gly Pro Thr Thr
145                 150                 155                 160

Phe Leu Pro Ser Leu Thr Val Gln Val Ala Met Ala Gly Ala Met Leu
                165                 170                 175

Ile Gly Leu His His Arg Ile Cys Tyr Thr Thr Ser Ala Ser Val Leu
                180                 185                 190

Thr Glu Ala Val Lys Gln Pro Asp Leu Pro Ser Gly Tyr Asp His Leu
            195                 200                 205

Cys Gln Phe Val Met Ser Gly Gln Leu Ser Asp Ser Glu Lys Leu Leu
        210                 215                 220

Glu Ser Leu Glu Asn Phe Trp Asn Gly Val Gln Glu Trp Thr Glu Arg
225                 230                 235                 240

His Gly Tyr Ile Val Asn Val Ser Lys Arg Ile Pro Phe
                245                 250

<210> SEQ ID NO 15
<211> LENGTH: 253
<212> TYPE: PRT
<213> ORGANISM: Artificial Sequence
<220> FEATURE:
<223> OTHER INFORMATION: Description of Artificial Sequence: Mutant
      enzyme obtained by introduction of point mutation into
      wild type KNT gene of Staphylococcus aureus and
      its expression

<400> SEQUENCE: 15

Met Ser Gly Pro Ile Ile Met Thr Arg Glu Glu Arg Met Lys Ile Val
1               5                   10                  15

His Glu Ile Lys Glu Arg Ile Leu Asp Lys Tyr Gly Asp Asp Val Lys
                20                  25                  30

Ala Ile Gly Val Tyr Gly Ser Leu Gly Arg Gln Thr Asp Gly Pro Tyr
            35                  40                  45

Ser Asp Ile Glu Met Met Cys Val Met Ser Thr Glu Gly Ala Glu Phe
        50                  55                  60

Ser Tyr Glu Trp Thr Thr Gly Glu Trp Lys Ala Glu Val Asn Phe Tyr
65                  70                  75                  80

Ser Glu Glu Ile Leu Leu Asp Tyr Ala Ser Arg Val Glu Ser Asp Trp
                85                  90                  95

Pro Leu Thr His Gly Arg Phe Ser Ile Leu Pro Ile Tyr Asp Pro
                100                 105                 110

Gly Gly Tyr Phe Glu Lys Val Tyr Gln Thr Ala Lys Ser Val Glu Ala
            115                 120                 125

Gln Lys Phe His Asp Ala Ile Cys Ala Leu Ile Val Glu Glu Leu Phe
        130                 135                 140

Glu Tyr Ala Gly Lys Trp Arg Asn Ile Arg Val Gln Gly Pro Thr Thr
145                 150                 155                 160

Phe Leu Pro Ser Leu Thr Val Gln Val Ala Met Ala Gly Ala Met Leu
                165                 170                 175

Ile Gly Leu His His Arg Ile Cys Tyr Thr Thr Ser Ala Thr Val Leu
```

180                 185                 190
Thr Glu Ala Val Lys Leu Ser Asp Leu Pro Ser Gly Tyr Asp His Leu
                195                 200                 205

Cys Gln Phe Val Met Ser Gly Gln Leu Ser Asp Ser Glu Lys Leu Leu
            210                 215                 220

Glu Ser Leu Glu Asn Phe Trp Asn Gly Val Gln Glu Trp Thr Glu Arg
225                 230                 235                 240

His Gly Tyr Ile Val Asp Val Ser Lys Arg Ile Pro Phe
                245                 250

<210> SEQ ID NO 16
<211> LENGTH: 253
<212> TYPE: PRT
<213> ORGANISM: Artificial Sequence
<220> FEATURE:
<223> OTHER INFORMATION: Description of Artificial Sequence: Mutant
      enzyme obtained by introduction of point mutation into
      wild type KNT gene of Staphylococcus aureus and
      its expression

<400> SEQUENCE: 16

Met Asn Gly Pro Ile Ile Met Thr Arg Glu Glu Arg Met Lys Ile Val
  1               5                  10                  15

His Glu Ile Lys Glu Arg Ile Leu Asp Lys Tyr Gly Asp Asp Val Lys
                 20                  25                  30

Ala Ile Gly Val Tyr Gly Ser Leu Gly Arg Gln Thr Asp Gly Pro Tyr
             35                  40                  45

Ser Asp Ile Glu Met Met Cys Val Met Ser Thr Glu Glu Thr Glu Phe
 50                  55                  60

Ser Tyr Glu Trp Thr Thr Gly Glu Trp Lys Ala Glu Val Asn Phe Tyr
 65                  70                  75                  80

Ser Glu Glu Ile Leu Leu Asp Tyr Ala Ser Arg Val Glu Pro Asp Trp
                 85                  90                  95

Pro Leu Thr His Gly Lys Phe Phe Ser Ile Leu Pro Ile Tyr Asp Thr
            100                 105                 110

Gly Gly Tyr Leu Glu Lys Val Tyr Gln Thr Ala Lys Ser Val Glu Ala
        115                 120                 125

Gln Lys Phe His Asp Ala Ile Cys Ala Leu Ile Val Glu Glu Leu Phe
130                 135                 140

Glu Tyr Ala Gly Lys Trp Arg Asn Ile Arg Val Gln Gly Pro Leu Thr
145                 150                 155                 160

Phe Leu Pro Ser Leu Thr Val Gln Val Ala Met Ala Gly Ala Met Leu
                165                 170                 175

Ile Gly Leu His His Arg Ile Cys Tyr Thr Thr Gly Ala Ser Val Leu
            180                 185                 190

Thr Glu Ala Val Arg Gln Pro Asp Leu Pro Pro Gly Tyr Asp His Leu
        195                 200                 205

Cys Gln Phe Val Met Ser Gly Gln Leu Ser Asp Ser Glu Lys Leu Leu
    210                 215                 220

Glu Ser Leu Glu Asn Phe Trp Asn Gly Ile Gln Glu Trp Ala Glu Arg
225                 230                 235                 240

His Gly Tyr Ile Val Asp Val Ser Lys Arg Ile Pro Phe
                245                 250

<210> SEQ ID NO 17
<211> LENGTH: 253
<212> TYPE: PRT

```
<213> ORGANISM: Artificial Sequence
<220> FEATURE:
<223> OTHER INFORMATION: Description of Artificial Sequence: Mutant
      enzyme obtained by introduction of point mutation into
      wild type KNT gene of Staphylococcus aureus and
      its expression

<400> SEQUENCE: 17
```

| Met | Asn | Gly | Pro | Ile | Ile | Met | Thr | Arg | Glu | Glu | Arg | Met | Lys | Ile | Val |
|---|---|---|---|---|---|---|---|---|---|---|---|---|---|---|---|
| 1 | | | | 5 | | | | | 10 | | | | | 15 | |

| His | Glu | Ile | Lys | Glu | Arg | Ile | Leu | Asp | Lys | Tyr | Gly | Asp | Asp | Val | Lys |
|---|---|---|---|---|---|---|---|---|---|---|---|---|---|---|---|
| | | | 20 | | | | | 25 | | | | | 30 | | |

| Ala | Ile | Gly | Val | Tyr | Gly | Ser | Leu | Gly | Arg | Gln | Thr | Asp | Gly | Pro | Tyr |
|---|---|---|---|---|---|---|---|---|---|---|---|---|---|---|---|
| | | 35 | | | | | 40 | | | | | 45 | | | |

| Ser | Asp | Ile | Glu | Met | Met | Cys | Val | Met | Ser | Thr | Glu | Gly | Ala | Glu | Phe |
|---|---|---|---|---|---|---|---|---|---|---|---|---|---|---|---|
| 50 | | | | | 55 | | | | | 60 | | | | | |

| Ser | Tyr | Glu | Trp | Thr | Thr | Gly | Glu | Trp | Lys | Ala | Glu | Val | Asn | Phe | Tyr |
|---|---|---|---|---|---|---|---|---|---|---|---|---|---|---|---|
| 65 | | | | | 70 | | | | | 75 | | | | | 80 |

| Ser | Glu | Glu | Ile | Leu | Leu | Asp | Tyr | Ala | Ser | Arg | Val | Glu | Ser | Asp | Trp |
|---|---|---|---|---|---|---|---|---|---|---|---|---|---|---|---|
| | | | | 85 | | | | | 90 | | | | | 95 | |

| Pro | Leu | Thr | His | Gly | Arg | Phe | Phe | Ser | Ile | Leu | Pro | Ile | Tyr | Asp | Pro |
|---|---|---|---|---|---|---|---|---|---|---|---|---|---|---|---|
| | | | 100 | | | | | 105 | | | | | 110 | | |

| Gly | Gly | Tyr | Phe | Glu | Lys | Val | Tyr | Gln | Thr | Ala | Lys | Ser | Val | Glu | Ala |
|---|---|---|---|---|---|---|---|---|---|---|---|---|---|---|---|
| | | 115 | | | | | 120 | | | | | 125 | | | |

| Gln | Lys | Phe | His | Asp | Ala | Ile | Cys | Ala | Leu | Ile | Val | Glu | Glu | Leu | Phe |
|---|---|---|---|---|---|---|---|---|---|---|---|---|---|---|---|
| 130 | | | | | 135 | | | | | 140 | | | | | |

| Glu | Tyr | Ala | Gly | Lys | Trp | Arg | Asn | Ile | Arg | Val | Gln | Gly | Pro | Thr | Thr |
|---|---|---|---|---|---|---|---|---|---|---|---|---|---|---|---|
| 145 | | | | | 150 | | | | | 155 | | | | | 160 |

| Phe | Leu | Pro | Ser | Leu | Thr | Val | Gln | Val | Ala | Met | Ala | Gly | Ala | Met | Leu |
|---|---|---|---|---|---|---|---|---|---|---|---|---|---|---|---|
| | | | | 165 | | | | | 170 | | | | | 175 | |

| Ile | Gly | Leu | His | His | Arg | Ile | Cys | Tyr | Thr | Thr | Ser | Ala | Ser | Val | Leu |
|---|---|---|---|---|---|---|---|---|---|---|---|---|---|---|---|
| | | | 180 | | | | | 185 | | | | | 190 | | |

| Thr | Glu | Ala | Val | Lys | Gln | Pro | Asp | Leu | Pro | Ser | Gly | Tyr | Val | Gln | Leu |
|---|---|---|---|---|---|---|---|---|---|---|---|---|---|---|---|
| | | 195 | | | | | 200 | | | | | 205 | | | |

| Cys | Gln | Phe | Val | Met | Ser | Gly | Gln | Leu | Ser | Asp | Ser | Glu | Lys | Leu | Leu |
|---|---|---|---|---|---|---|---|---|---|---|---|---|---|---|---|
| 210 | | | | | 215 | | | | | 220 | | | | | |

| Glu | Ser | Leu | Glu | Asn | Phe | Trp | Asn | Gly | Ile | Gln | Glu | Trp | Thr | Glu | Arg |
|---|---|---|---|---|---|---|---|---|---|---|---|---|---|---|---|
| 225 | | | | | 230 | | | | | 235 | | | | | 240 |

| His | Gly | Tyr | Ile | Val | Asp | Val | Ser | Lys | Arg | Ile | Pro | Phe |
|---|---|---|---|---|---|---|---|---|---|---|---|---|
| | | | | 245 | | | | | 250 | | | |

```
<210> SEQ ID NO 18
<211> LENGTH: 253
<212> TYPE: PRT
<213> ORGANISM: Artificial Sequence
<220> FEATURE:
<223> OTHER INFORMATION: Description of Artificial Sequence: Mutant
      enzyme obtained by introduction of point mutation into
      wild type KNT gene of Staphylococcus aureus and
      its expression

<400> SEQUENCE: 18
```

| Met | Asn | Gly | Pro | Ile | Ile | Met | Thr | Arg | Glu | Glu | Arg | Met | Lys | Ile | Val |
|---|---|---|---|---|---|---|---|---|---|---|---|---|---|---|---|
| 1 | | | | 5 | | | | | 10 | | | | | 15 | |

| His | Glu | Ile | Lys | Glu | Arg | Ile | Leu | Asp | Lys | Tyr | Gly | Asp | Asp | Val | Lys |
|---|---|---|---|---|---|---|---|---|---|---|---|---|---|---|---|
| | | | 20 | | | | | 25 | | | | | 30 | | |

| Ala | Ile | Gly | Val | Tyr | Gly | Ser | Leu | Gly | Arg | Gln | Thr | Asp | Gly | Pro | Tyr |
|---|---|---|---|---|---|---|---|---|---|---|---|---|---|---|---|
| | | 35 | | | | | 40 | | | | | 45 | | | |

```
Ser Asp Ile Glu Met Met Cys Val Met Ser Thr Glu Gly Ala Glu Phe
     50                  55                  60

Ser Tyr Glu Trp Thr Thr Gly Glu Trp Lys Ala Glu Val Asn Phe Tyr
 65                  70                  75                  80

Ser Glu Glu Ile Leu Leu Asp Tyr Ala Ser Arg Val Glu Ser Asp Trp
                 85                  90                  95

Pro Leu Thr His Gly Arg Phe Phe Ser Ile Leu Pro Ile Tyr Asp Pro
                100                 105                 110

Gly Gly Tyr Phe Glu Lys Val Tyr Gln Thr Ala Lys Ser Val Glu Ala
                115                 120                 125

Gln Lys Phe His Asp Ala Ile Cys Ala Leu Ile Val Glu Glu Leu Phe
    130                 135                 140

Glu Tyr Ala Gly Lys Trp Arg Asn Ile Arg Val Gln Gly Pro Thr Thr
145                 150                 155                 160

Phe Leu Pro Ser Leu Thr Val Gln Val Ala Met Ala Gly Ala Met Leu
                165                 170                 175

Ile Gly Leu His His Arg Ile Cys Tyr Thr Thr Ser Ala Ser Val Leu
                180                 185                 190

Thr Glu Ala Val Lys Gln Pro Asp Leu Pro Ser Gly Tyr Val Gln Leu
        195                 200                 205

Cys Gln Phe Val Met Ser Gly Gln Leu Ser Asp Ser Glu Lys Leu Leu
210                 215                 220

Glu Ser Leu Glu Asn Phe Trp Asn Gly Ile Gln Glu Trp Thr Glu Arg
225                 230                 235                 240

His Gly Tyr Ile Val Asp Val Ser Lys Arg Ile Pro Phe
                245                 250

<210> SEQ ID NO 19
<211> LENGTH: 253
<212> TYPE: PRT
<213> ORGANISM: Artificial Sequence
<220> FEATURE:
<223> OTHER INFORMATION: Description of Artificial Sequence: Mutant
      enzyme obtained by introduction of point mutation into
      wild type KNT gene of Staphylococcus aureus and
      its expression

<400> SEQUENCE: 19

Met Asn Gly Pro Ile Ile Met Thr Arg Glu Glu Arg Met Lys Ile Val
  1               5                  10                  15

His Glu Ile Lys Glu Arg Ile Leu Asp Lys Tyr Gly Asp Asp Val Lys
             20                  25                  30

Ala Ile Gly Val Tyr Gly Ser Leu Gly Arg Gln Thr Asp Gly Pro Tyr
         35                  40                  45

Ser Asp Ile Glu Met Met Cys Val Met Ser Thr Glu Gly Ala Glu Phe
     50                  55                  60

Ser Tyr Glu Trp Thr Thr Gly Glu Trp Lys Ala Glu Val Asn Phe Tyr
 65                  70                  75                  80

Ser Glu Glu Ile Leu Leu Asp Tyr Ala Ser Arg Val Glu Pro Asp Trp
                 85                  90                  95

Pro Leu Thr His Gly Lys Phe Phe Ser Ile Leu Pro Ile Tyr Asp Pro
                100                 105                 110

Gly Gly Tyr Leu Glu Lys Val Tyr Gln Thr Ala Lys Ser Val Glu Ala
                115                 120                 125

Gln Lys Phe His Asp Ala Ile Cys Ala Leu Ile Val Glu Glu Leu Phe
    130                 135                 140
```

```
Glu Tyr Ala Gly Lys Trp Arg Asn Ile Arg Val Gln Gly Pro Thr Thr
145                 150                 155                 160

Phe Leu Pro Ser Leu Thr Val Gln Val Ala Met Ala Gly Ala Met Leu
                165                 170                 175

Ile Gly Leu His His Arg Ile Cys Tyr Thr Thr Ser Ala Ser Val Leu
                180                 185                 190

Thr Glu Ala Val Lys Gln Pro Asp Leu Pro Ser Gly Tyr Val Gln Leu
                195                 200                 205

Cys Gln Phe Val Met Ser Gly Gln Leu Ser Asp Pro Glu Lys Leu Leu
210                 215                 220

Glu Ser Leu Glu Asn Phe Trp Asn Gly Ile Gln Glu Trp Thr Glu Arg
225                 230                 235                 240

His Gly Tyr Ile Val Asp Val Ser Lys Arg Ile Pro Phe
                245                 250

<210> SEQ ID NO 20
<211> LENGTH: 253
<212> TYPE: PRT
<213> ORGANISM: Artificial Sequence
<220> FEATURE:
<223> OTHER INFORMATION: Description of Artificial Sequence: Mutant
      enzyme obtained by introduction of point mutation into
      wild type KNT gene of Staphylococcus aureus and
      its expression

<400> SEQUENCE: 20

Met Asn Gly Pro Ile Ile Met Thr Arg Glu Glu Arg Met Lys Ile Val
1               5                   10                  15

His Glu Ile Lys Glu Arg Ile Leu Asp Lys Tyr Gly Asp Asp Val Lys
                20                  25                  30

Ala Ile Gly Val Tyr Gly Ser Leu Gly Arg Gln Thr Asp Gly Pro Tyr
            35                  40                  45

Ser Asp Ile Glu Met Met Cys Val Leu Ser Thr Glu Glu Ala Glu Phe
    50                  55                  60

Ser Tyr Glu Trp Thr Thr Gly Glu Trp Lys Ala Glu Val Asn Phe Tyr
65                  70                  75                  80

Ser Glu Glu Ile Leu Leu Asp Tyr Ala Ser Arg Val Glu Pro Asp Trp
                85                  90                  95

Pro Leu Thr His Gly Lys Phe Phe Ser Ile Leu Pro Ile Tyr Asp Pro
                100                 105                 110

Gly Gly Tyr Leu Glu Lys Val Tyr Gln Thr Ala Lys Ser Val Glu Ala
            115                 120                 125

Gln Lys Phe His Asp Ala Ile Cys Ala Leu Ile Val Glu Glu Leu Phe
130                 135                 140

Glu Tyr Ala Gly Lys Trp Arg Asn Ile Arg Val Gln Gly Pro Thr Thr
145                 150                 155                 160

Phe Leu Pro Ser Leu Thr Val Gln Val Ala Met Ala Gly Ala Met Leu
                165                 170                 175

Ile Gly Leu His His Arg Ile Cys Tyr Thr Thr Ser Ala Ser Val Leu
                180                 185                 190

Thr Glu Ala Val Lys Gln Pro Asp Leu Pro Ser Gly Tyr Val Gln Leu
                195                 200                 205

Cys Gln Phe Val Met Ser Gly Gln Leu Ser Asp Ser Glu Lys Leu Leu
210                 215                 220
```

```
Glu Ser Leu Glu Asn Phe Trp Asn Gly Ile Gln Glu Trp Thr Glu Arg
225                 230                 235                 240

His Gly Tyr Ile Val Asp Val Ser Lys Arg Ile Pro Phe
                245                 250
```

MUTANT KANAMYCIN NUCLEOTIDYLTRANSFERASES FROM *S. AUREUS*

FIELD OF THE INVENTION

The present invention relates to a novel kanamycin nucleotidyltransferase with markedly improved thermostability, a selective marker using the same, and a screening method for thermophilic bacteria such as *Thermus thermophilus* using said selective marker.

BACKGROUND OF THE INVENTION

Thermophilic bacteria have attracted attention due to the applicability of their proteins in biotechnology. Since the proteins are stable at extremes of pH, they crystallize easily in comparison to non-thermophilic proteins, are easy to handle, and are useful as a good research material in the study of interrelation between enzyme structure and its function. However, when thermophilic protein is expressed in *E. coli*, its natural conformation may not be reproduced. These proteins, since standard tools of genetic engineering cannot be employed, cannot be expressed in thermophilic bacteria at high temperatures. This prevents an examination of the biological role of these proteins by knocking out genes with functions that cannot be predicted from the sequence data obtained from the genome project, followed by their reintroduction. *Thermus thermophilus*, which belongs to a Eubacterium, is an attractive organism which can be grown at the highest temperatures (50–82° C.) among organisms whose molecular biology is under study.

The sequence analysis of the entire genome of highly thermophilic *Thermus thermophilus* is currently in progress. Sequence research on the entire genome will soon be completed in Japan (HB8 strain) and Germany (HB27 strain). As with other genome projects, main interest is not in the sequence itself, but has shifted to functional or structural genomics, which is post-sequencing research.

There is a project to organizationally research the structure and biological function of *T. thermophilus* protein. Therefore, there is a need to rapidly develop genetic engineering tools. The most indispensable tool is an easy-to-use selective marker.

Until now, there were only 2 selective systems that could be used with *T. thermophilus*. One system was a method where an auxotrophic host was selected via a plasmid into which the corresponding gene was incorporated. However, the auxotrophic marker is inconvenient for routine use. This is because, preparation of the selection medium is troublesome, and growth of cells on the nutritionally restricted plate, is slow even under the optimal growth temperature.

Another system used a kanamycin nucleotidyltransferase (KNT) gene that could be used only at under 60° C. *T. thermophilus* has sensitivity to general antibiotics, however, the only antibiotic resistant marker that can be used with *T. thermophilus* is a mutant gene of *Staphylococcus aureus* KNT. However, since this mutant KNT cannot be used at over 60° C. as a selective marker, it is far from ideal. At this temperature which is far below optimal growth temperature (70–75° C.), cell growth is extremely slow. Thus, we began work to improve the thermostability of KNT.

BRIEF SUMMARY OF THE INVENTION

Many attempts have been made to improve the thermostability of proteins. Most attempts were designed rationally based on an understanding of the protein folding and structure formation. For example, the introduction of disulfide bonds, re-sequencing of packing of hydrophobic cores and substitution with proline were attempted. To investigate whether it was possible to realize thermostability through amino acid substitution, a comparison was made of the sequences of homologous proteins of thermophilic and non-thermophilic bacteria. In contrast, irrational methods have also been applied in order to increase thermostability of proteins. Most of this research involved the induction of random mutations followed by a single screening in place of directed evolution which comprises repeating cycles of inducing mutation, selecting, and amplifying the selected mutant. Only 2 or 3 cases of research reported successful improvement of thermostability through directed evolution.

The present inventors employing a strategy based on directed evolution toward the upper limit of the growth temperature of *T. thermophilus*, have succeeded in increasing the thermostability of a kanamycin resistant gene product to the upper limit of the growth temperature. The resultant KNT is a convenient selective marker of thermophilic bacteria such as *T. thermophilus*.

In other words, the present invention provides the following (1)–(9):

(1) A mutant kanamycin nucleotidyltransferase having one or more point mutations selected from a group consisting of Met57Leu, Ala62Val, Ser94Pro, Ser203Pro, Asp206Val, His207Gln, Ser220Pro, Ile234Val and Thr238Ala as against the protein comprising the amino acid sequence indicated by SEQ ID NO: 1, and having improved thermostability.

(2) A mutant kanamycin nucleotidyltransferase with improved thermostability, wherein it comprises the amino acid sequence indicated by SEQ ID NO: 2.

(3) The kanamycin nucleotidyltransferase according to (1) above, wherein it comprises the amino acid sequence indicated in SEQ ID NO: 3.

(4) A kanamycin nucleotidyltransferase gene encoding the kanamycin nucleotidyltransferase according to any one of (1) to (3) above.

(5) A plasmid comprising the gene according to (4) above.

(6) A transformant comprising the plasmid according to (5) above.

(7) A selective marker for thermophilic bacteria characterized in that it is the gene according to (4) above.

(8) A method for screening thermophilic bacteria wherein the selective marker according to (7) above is used.

(9) The screening method according to (8) above, wherein said thermophilic bacteria is *Thermus thermophilus*.

In the present invention, the mutant strain with the greatest thermostability has 19 amino acid substitutions when compared with the form prior to mutation. Thermostability was increase by 20° C., however, no great change in enzyme activity per se was observed. Most of the altered residues reside on the surface of the protein molecule. Interestingly, 5 substitutions out of 19 were substitutions of the existing residue by proline. The evolved kanamycin-resistant gene product is capable of becoming a selective marker at the optimum growth temperature of *T. thermophilus*. The development of such convenient genetic engineering tools will promote the post-sequencing research of *T. thermophilus*.

(A) The heat denaturation of WT* (□), KT3-11 (Δ) and HTK (○) was monitored on a CD at 222 nm and recorded. Measurement conditions were: protein concentration 0.8 μM; 50 mM potassium phosphate buffer containing 0.1 M KCl; and pH of 7.0.

Degree of Denaturation $(\%)=(\theta^T_{222}-\theta^N_{222})/(\theta^D_{222}-\theta^N_{222})$ ($\theta^T_{222}$ is the average residue molecular ellipticity at T° C., at 222 nm and $\theta^N_{222}$ and $\theta^D_{222}$ are the average residue molecular ellipticities at 222 nm for the non-denatured and denatured enzyme, respectively.)

(B) Heat Inactivation: Enzyme solution is heated for ten minutes at the designated temperature. After cooling, activity is measured at 25° C. Heat treatment was conducted with a protein concentration of 1.2 μM and using the same buffer as in the CD measurement. The values for each enzyme are expressed as a ratio in comparison to the respective non-heat-treated enzyme. Each numerical value has a standard deviation of ±10%

Figure 3:
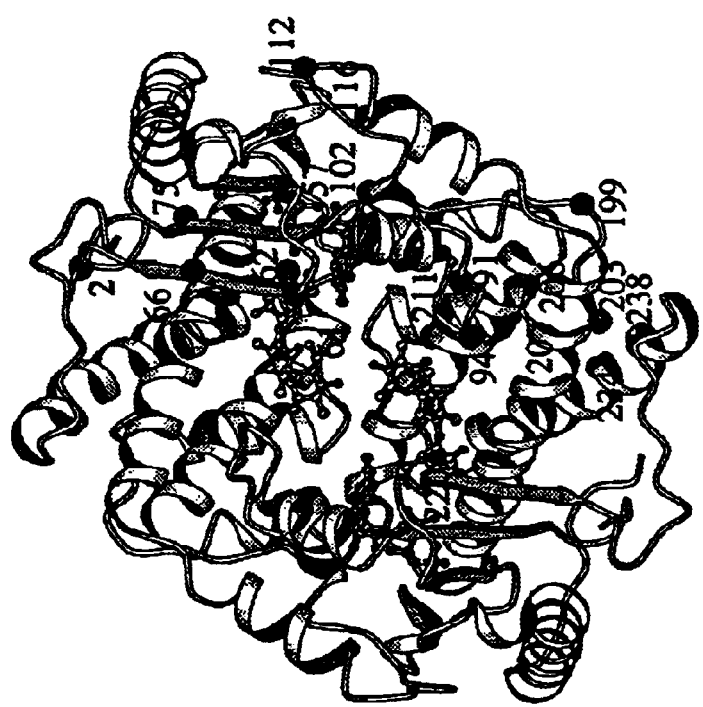
Figure 3:
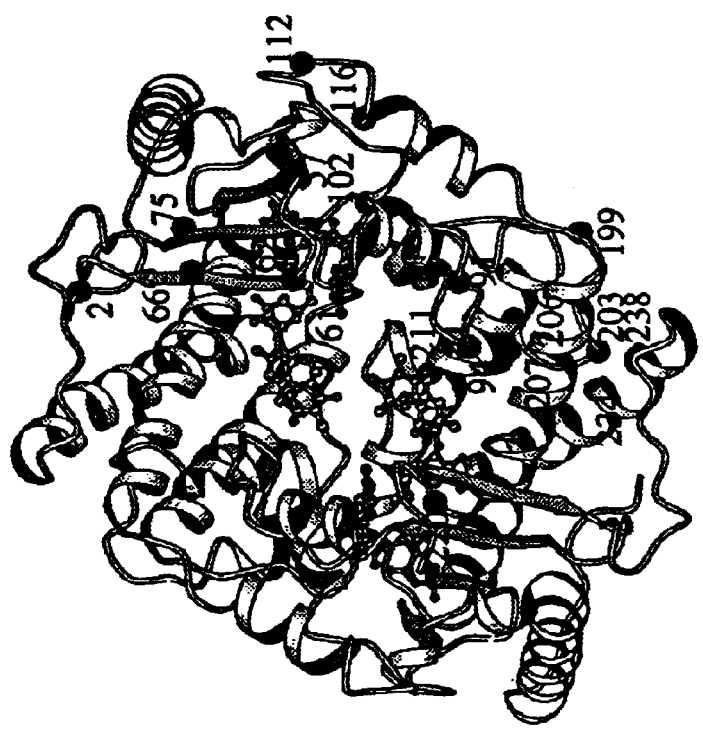

FIG. 3 indicates a 3-dimensional representation of the structure of KNT having the Asp80Tyr mutation (KT3-11 and HTK). KNT is a homodimer, and the positions and the residue numbers of modified residues are indicated for only one of the subunits. The mutated residues of KT3-11, the additional 9 mutated residues of HTK, kanamycin, and adenosine 5'-α, β-methylene triphosphate which is an analog of ATP, are indicated. This figure was prepared using MOLSCRIPT (Per Kraulis, Department of Molecular Biology. Uppsala University, Sweden.)

Figure 4:
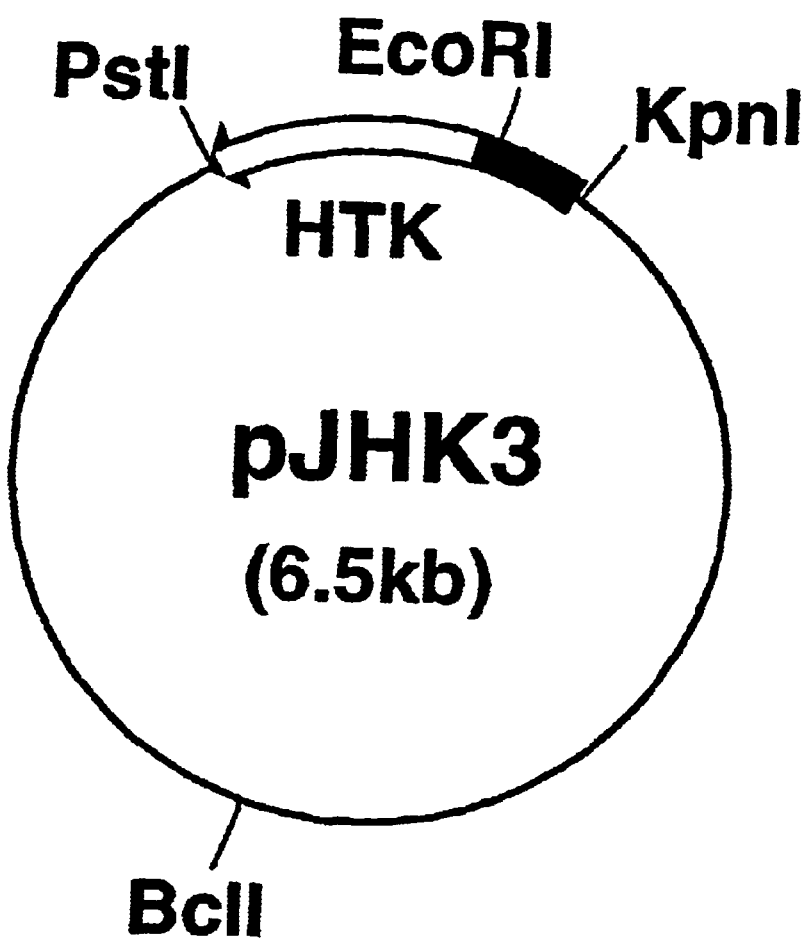

FIG. 4 indicates a restriction map for plasmid pHJK3.

DETAILED DESCRIPTION OF THE INVENTION

Below, a working embodiment of the present invention will be explained, but this is not intended to limit the present invention to only the form described herein. Suitable modifications or alterations that could easily be made by a person skilled in the art based on the descriptions contained herein or known techniques in the art, should be contained within the range of the present invention.

In the present specification, the term "directed evolution" refers to means by which the target function is improved through repetitive conduct of the following steps: introduction of a mutation, selection, amplification of the selected mutant, and the further introduction of a mutation into this mutant.

Further, in the present specification, a description concerning amino acid substitution, e.g. "Met57Leu", means that the Met at position 57 of the wild type (referred to in this specification as "WT*") is replaced by Leu.

Further, in the present specification, "improved thermostability" refers to the retention of enzyme activity under such high temperature conditions that the wild type protein would be denatured and enzyme activity would be lost.

Medium

T. thermophilus cells are preferably cultured in a liquid medium comprising 0.4% trypton, 0.2% yeast extract and 0.1% NaCl (pH 7.5). In the selection of the T. thermophilus transformant strain, a 3% agar plate medium comprising 50 μg/ml kanamycin (where the temperature is under 70° C.), or a 1.5% gellan gum plate medium comprising 500μg/ml kanamycin (where the temperature is over 70° C.), is used. To solidify the gellan gum, bivalent cations 1.5 mM CaCl$_2$ and 1.5 mM MgCl, are added. Since these ions antagonize the kanamycin, the concentration of kanamycin in the gellan gum medium is set higher.

Construction of Plasmid pJHK1

Figure 1A:
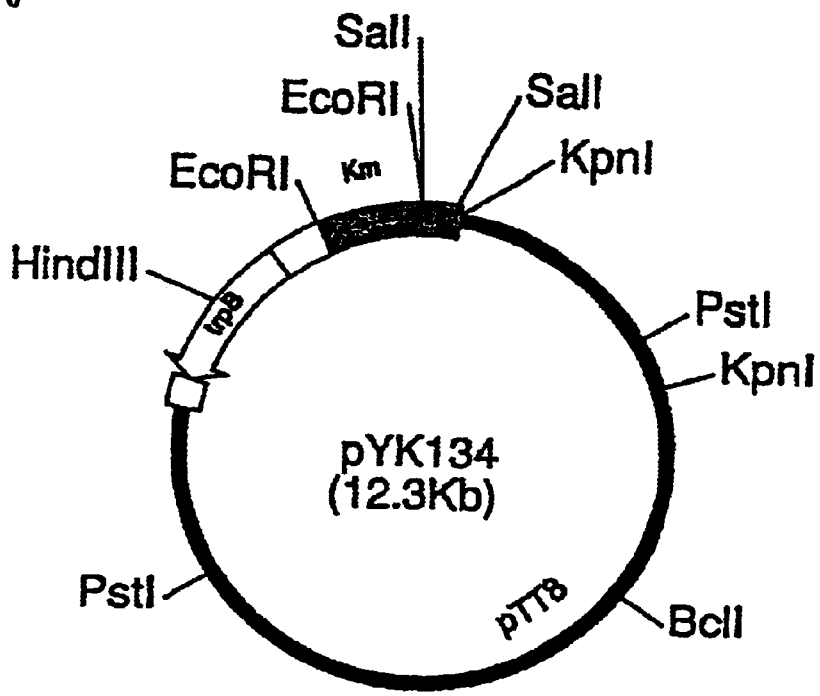
FIG. 1 indicates the restriction maps for each of plasmids (a) pYK134, (b)pTT8, and (c)pJHK1.
Figure 1B:
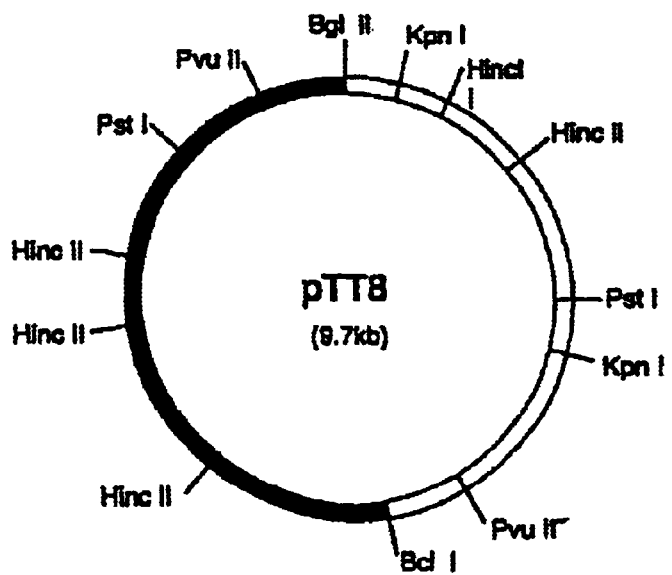
Figure 1C:
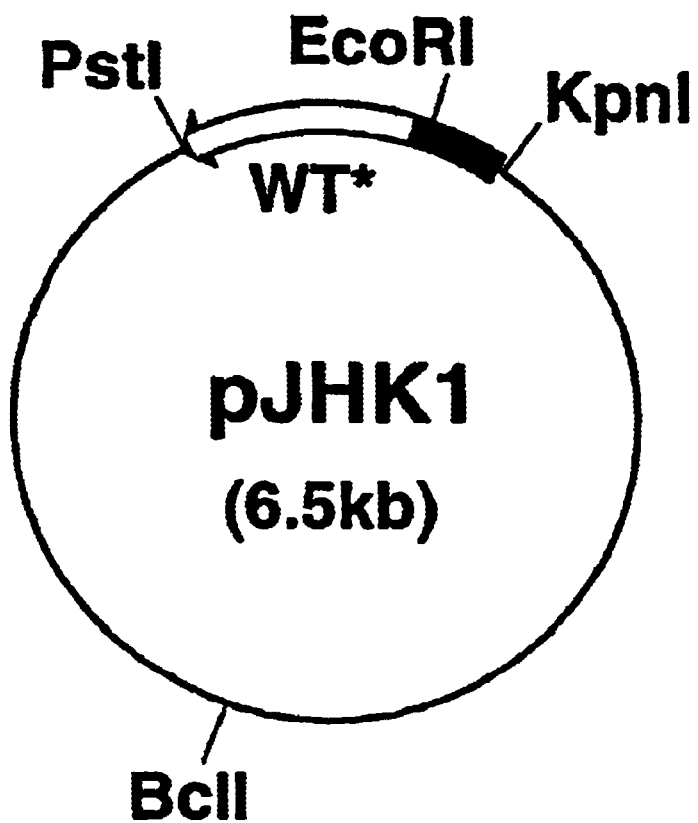

The nucleotide sequence and amino acid sequence of the wild type KNT of *Staphylococcus aureus* (SEQ ID NO: 10 and 11) are known from Nakanishi, K. et al, J. Ferment. Technol. 54: 801–807 (1976), etc. A plasmid encoding the protein includes pUB110 (3,000 kDa, Lacey, R. W. and I. Chopra, J. Med. Microbiol., 7: 285–297 (1974))). Directed evolution is initiated from a mutant (denoted "WT*", SEQ ID NO:1) having two substitutions (Asp80Tyr and Thr130Lys) in relation to the wild type KNT. The WT*KNT gene is amplified by PCR from pYK134 (12.3 kb, National Institute of Bioscience and Human-Technology, from Dr. Y. Koyama) using two primers (5'-primer: 5'-GACTGTACG GGTACCCGTTGACGGCGGATATGGTA-3' (The underlined portion is the Kpn I site, SEQ ID NO: 4) and 3'primer: 5'-GACTGTACG CTGCAGCGTAACCAACATGATTAACA-3' (The underlined portion is the Pst I site, SEQ ID NO: 5)). Said pYK134 is derived from plasmid PTT8 separated from *T. thermophilus* HB8 (Tokyo Pharmaceutical University, from Dr. Y. Oshima) and its ori is situated in the vicinity of a BclI site. In order to reduce the size of pTT8 (9.7 kb), a KpnI-PstI fragment (5.5 kb) comprising the BclI site is gel purified and ligated with the amplified WT* gene. The obtained plasmid pJHK1 (6.5 kb) is used in the directed evolution experiment. A restriction map for said pYK134, pTT8 and pJHK1, is shown in FIG. 1.

Transformation of *T. thermophilus* HB27

Transformation of *T. thermophilus* is preferably performed as follows: *T. thermophilus* which has been cultured overnight is diluted by a factor of 100 in a new medium comprising 0.4 mM CaCl$_2$ and 0.4 mM MgCl$_2$ then shake cultured for 2 hours at 70° C. The culture product (1×10$^8$ cells/ml) is mixed with a plasmid, e.g. pJHK1 and incubated with agitation for two hours at 70° C., then sprinkled on an plate medium comprising kanamycin.

Directed Evolution of Thermostable KNT Mutant

DNA shuffling is performed in the manner described by Stemmer et al (Stemmer, W. P. C. et al, Nature, 370, 389–391 (1994)). In practice, the DNA comprising the target gene is fragmented using DNaseI and DNA fragments of 100–300 bp are recovered. A mixture of these DNA fragments is amplified by PCR without primers. Here, since there exist overlapping sequences between the various fragments, the pre-fragmentation full-length DNA is reconstructed This full length DNA is then amplified by PCR using 5' and 3' terminal primers.

The coding region of the WT*gene is PCR amplified from the above obtained pJHK1. The 5' primer used in PCR is 5'-GACTGTACG GAATTCGAGCTCGAGCAAATCTAAAA-3' (the underlined portion is the EcoRI site, SEQ ID NO: 6) and the sequence of the 3' primer is as above (SEQ ID NO: 5). The shuffled fragments are cleaved with EcoRI and PstI, purified and introduced into pJHK1 which was cleaved with the same restriction enzymes. Thereafter, *T. thermophilus* HB27 (National Institute of Bioscience and Human-Technology, from Dr. Y. Koyama) is transformed with this pJHK1 derivative (inserted with shuffled fragment). The transformant (library) is screened on a plate containing kanamycin (64° C., 36 hrs), positive colonies taken, and transferred to a kanamycin plate and cultured at 64° C., for 40 hours. From the plate, cells are collected with sterilized water and a plasmid mixture—pKT1 mix is prepared. The mutant gene amplified from the pKT1 mix, is then shuffled, and subjected to a second screening as with the first time. That is, the library obtained by shuffling is cultured for 40 hours at 69° C., and once more the positive colonies are selected. This is denoted a pKT2 mix. pKT3 is prepared from the positive colonies obtained from the third screening. Culturing is conducted for 20 hours at 79° C. $T.$ $thermophilus$ HB27 is transformed with pKT3 mix, and after culturing for 40 hours at 81° C., then the largest colonies, for example about 20, are picked up, cultured, and plasmid (pKT3-1-3-20) is prepared. The coding regions of each plasmid are amplified, subcloned to the KpnI and PstI sites of pUC18 (TAKARA), and allowed to express in $E.$ $coli.$ The $E.$ $coli$ culture lysate is heated at 70° C. for 10 min, and the residual KNT activity of the 20 KT3 mutant strains are compared to one another. The ten strains having the highest residual activity are selected and their coding regions sequenced.

Expression and Purification of KNT

Expression plasmid pUT7 is constructed by linking PvuII-ScaI fragment of pUC18 including ori, and the BglII-ScaI fragment of pET21b (Novagen) including a T7 promoter. Plasmids suitable for expression of KNT include any plasmids that are capable of self-replication in a host cell and can be incorporated into a chromosome, and comprise a promoter situated such that the KNT gene can be transcribed, and are otherwise not especially limited. The mutant KNT gene amplified by PCR is subcloned to the NdeI and XhoI sites of pUT7. The primers used here are, '5 primers; 5'-GACTGTACG CATATGAATGGACCAATAATAATGAC-3' (used for WT*, the underlined portion is the NdeI site, SEQ ID NO: 7) and 5'-GACTGTACG CATATGAAAGGACCAATAATAATGAC-3' (for KT3-11 and HTK, the underlined portion is the NdeI site, SEQ ID NO: 8) and, 3' primer: 5'-GACTGTACG CTCGAGCGTAACCAACATGATTAACA-3' (the underlined portion is the XhoI site, SEQ ID NO: 9). Here, the initiation codon of KNT is altered from GTG to ATG.

In the present invention, host cells for allowing expression of KNT gene include bacteria such as $E.$ $coli,$ yeast or animal cells, and insect cells, though the type of cell is not particularly limited. Where the host cell to be used is $E.$ $coli,$ $E.$ $coli$ BL21(DE3, pLysS) cells which comprise the obtained expression plasmid, are cultured overnight at 37° C. in a medium containing 1.0% polypeptone, 0.5% yeast extract, 1.0% NaCl (pH 7.0), 100 $\mu$g/ml ampicillin, and 1 mM isopropyl-1-thio-$\beta$-D-galactoside. Cells are collected, resuspended in a 20 mM Tris-HCl buffer (pH7.5) containing 50 mM NaCl and 2 mM mercaptoethanol, and disrupted by ultrasonification. The following procedures are performed at 4° C. After centrifuging, the supernatant of crude extract is loaded on a DEAE-Toyo Pearl column (Tosoh) equilibrated with the above-mentioned buffer and eluted with a 50–250 mM NaCl linear gradient. Each fraction is checked by KNT assay and by SDS-PAGE. Fractions containing KNT are collected and subjected to dialysis overnight against a 5 mM potassium phosphate buffer (pH 7.0) containing 2 mM of 2-mercaptoethanol. Dialysis fluid is then loaded on a hydroxy apatite column equilibrated with the dialysis buffer and eluted with a linear gradient of 5–100 mM potassium phosphate. The fractions including KNT are collected and concentrated by ultrafiltration. Next, the enzyme is purified by eluting the concentrated solution through a Sephacryl S-200 column (Amersham Pharmacia Biotech) equilibrated with a 20 mM potassium phosphate buffer (pH 7.0) containing 0.1 M KCl. Purification is continued until the purity exceeds 90% on SDS-PAGE.

KNT Assay $Staphylococcus$ $aureus$ KNT catalyzes the transfer of AMP from ATP to the 4'-hydroxy group of kanamycin. Enzyme activity is measured at 25° C. in a 50 mM Na-MES buffer (pH 6.0) containing 50 mM $MgCl_2$, 0.1–2 mM kanamycin and 0.4–5.4 mM [8-$^{14}$C] ATP (0.4–4 mCi/mmol). The reaction is stopped by adding a half amount of 6N HCl and is spotted on a PEI-cellulose TLC plate. The plate is developed for 45 min with a solvent consisting of 1-propanol/$H_2O$/acetic acid in a ratio of 60:39:1. The radioactivity of the formed kanamycin-[$^{14}$C]AMP is measured with Fujifilm Phosphorimager BAS-2000 (Fujifilm). In this system the RF value of the product is 0.3.

Heat Denaturation

The heat denaturation curve, is recorded in a 5 mm cuvette with a Jasco J-720WI spectropolarimeter (JASCO) having a PTC-348WI thermo-electrical temperature control system, over a temperature range of 30–90° C. (for HTK, 30–95° C.). The protein concentration is 0.8 $\mu$M and the buffer is 50 mM potassium phosphate containing 0.1 M KCl with a pH of 7.0. The temperature of the sample is increased by 1° C. per minute while monitoring at 222 nm.

EXAMPLES

Below, the present invention will be further explained by means of examples. However, this is not to limit the present invention to these examples.

Example 1

Directed Evolution

The first screening was performed as described below. A mutation was introduced into the WT* gene by DNA shuffling, the steps of which were explained above. From the $3.2 \times 10^6$ transformants screened at 64° C., 431 positive colonies were singled out. Finally, a plasmid mixture, pKT1 mix, was prepared from the positive colonies. The mutant KNT gene amplified from the pKT1 mix was subjected to further DNA shuffling in order to allow the mutant gene to recombine while accepting another point mutation. A second screening was performed at 69° C. (library size; $4.8 \times 10^6$, 109 colonies selected) and a third screening at 79° C. (library size: $2.4 \times 10^5$; 209 colonies selected.) $T.$ $thermophilus$ cells transformed with pKT3 mix formed colonies on a plate containing kanamycin at 81° C. However, since the host $T.$ $thermophilus$ cannot form colonies at a temperature higher than 81° C., a fourth screening was impossible.

Example 2

KT3 Mutant Strain

Twenty KT3 mutant strains obtained from large colonies during the screening at 81° C., were investigated in more detail. KT3 mutant strains (KT3-1 to KT3-20) were expressed in $E.$ $coli,$ respectively, and the thermostability of each strain was predicted from residual catalytic activity after heating the solution at 70° C. for 10 minutes. Based on this analysis, the 10 most stable strains of KT3 were selected and their DNA sequences were determined. (KT3-1 to KT3-19. See Table 1)

TABLE 1

Amino acid substitutions in the KNT mutant strains

| SEQ ID NO: | Residue NO. | 2 | 17 | 25 | 57 | 61 | 62 | 66 | 75 | 91 | 94 | 102 | 112 | 116 | 117 | 159 | 188 | 190 | 196 |
|---|---|---|---|---|---|---|---|---|---|---|---|---|---|---|---|---|---|---|---|
| 1 | WT* | N | H | D | M | E | A | H | V | Q | S | Q | S | L | E | T | S | S | V |
| 12 | KT3-1 | | Y | | | | | | A | R | | R | P | F | | | | | L |
| 13 | KT3-3 | | | N | L | G | V | | A | | P | R | | | G | | | L | |
| 14 | KT3-5 | | | | | G | | Y | A | R | P | R | | | | | | | |
| 15 | KT3-7 | S | | | | G | | Y | A | R | | R | P | F | | | | T | |
| 2 | KT3-11 | K | | | | G | | Y | A | R | | R | P | F | | | | | |
| 16 | KT3-12 | | | | | | T | Y | A | R | P | K | T | | | L | G | | |
| 17 | KT3-13 | | | | | G | | Y | A | R | | R | P | F | | | | | |
| 18 | KT3-15 | | | | | G | | Y | A | R | | R | P | F | | | | | |
| 19 | KT3-16 | | | | | G | | Y | A | R | P | K | P | | | | | | |
| 20 | KT3-19 | | | | L | | | Y | A | R | P | K | P | | | | | | |
| 3 | HTK | K | | | L | G | V | Y | A | R | P | R | P | F | | | | | |

| SEQ ID NO: | Residue NO. | 197 | 198 | 199 | 203 | 206 | 207 | 211 | 220 | 234 | 238 | 246 |
|---|---|---|---|---|---|---|---|---|---|---|---|---|
| 1 | WT* | K | Q | S | S | D | H | F | S | L | T | D |
| 12 | KT3-1 | | | | | | | | | V | A | |
| 13 | KT3-3 | | | | | | | L | | | | |
| 14 | KT3-5 | | | | P | | | | | V | | N |
| 15 | KT3-7 | | L | | | | | | | V | | |
| 2 | KT3-11 | | | | P | | | L | | | | |
| 16 | KT3-12 | R | | | P | P | | | | | A | |
| 17 | KT3-13 | | | | P | | V | Q | | | | |
| 18 | KT3-15 | | | | P | | V | Q | | | | |
| 19 | KT3-16 | | | | P | | V | Q | | P | | |
| 20 | KT3-19 | | | | P | | V | Q | | | | |
| 3 | HTK | | | | P | P | V | Q | L | P | V | A |

KT3-15 has the same mis-sense mutation as KT3-13. These two mutants, share three silent mutations, however KT3-13's two silent mutations and KT3-15's one mutation are mutually specific to each. Therefore, it is clear that these two mutants are distinct clones.

Each mutant strain had about 15 point mutations. Of these 4 to 5 were silent mutations. There is a possibility that the GC content of the KNT gene increases following high temperature screening, however, in the 39 silent mutations no specific trend toward G or C was observed. (No data). The Val75Ala substitution, which is a conserved substitution, was found in all ten strains of KT3 (Table 1). Other conserved substitutions were Glu61Gly found in 7 mutant strains, His66Tyr in 8 strains, Gln91Arg in 9 strains, Ser112Pro in 7 strains and Ser199Pro in 7 strains. In all of the KT3 strains investigated, Gln102 was substituted by basic amino acid (in 7 strains by Arg and in 3 strains by Lys). Interestingly, among the 29 substitutions, 5 were substitution by proline. Many examples of proline substitutions increasing the thermostability of proteins are known.

KT3-11, which had the highest thermostability among the 10 strains of KT3, was expressed in *E. coli* and purified. The purified KT3-11 (SEQ ID NO:2) had post-treatment (70° C., 10 min) activity, but it was completely lost at 75° C. (No data). However, plasmid pKT3-11 which comprises KT3-11 transforms *T. thermophilus* cells at 81° C. KT3-11 may have higher thermostability in cytoplasm, or it may be expressed rapidly to exhibit KNT activity.

Example 3

Creation of Mutant with Higher Thermostability

The directed evolution of example 2 was completed with three screenings and selections. If further screening were possible, a mutant with higher thermostability could have been obtained through recombination between the KT3 mutants. Therefore, to achieve further improvement of the thermostability of KT3-11, the following strategy was used. Mutations conserved in two or more of other KT3 strains, and mutations modified to proline, were selected. Since KT3-3 was particular among the KT3 mutants (Table 1), mutations found in KT3-3 but not in KT3-11 were also selected. These mutations were independently added to KT3-11 with an Amersham kit (Sculpter®). Each unitary mutant strain of KT3-11 was allowed to express in *E. coli*, and the thermostability of crude lysate of each mutant was compared to K3-11. As the results in Table 2 show, Each of the following nine mutations improved the thermostability of KT3-11: Met57Leu, Ala62Val, Ser94Pro, Ser203Pro, Asp206Val, His207Gln, Ser220Pro, Ile234Val, and Thr238Ala.

TABLE 2

Relative Residual Activity of KT3-11 Mutant Strains

| KT3-11 Mutant Strain | Relative Residual Activity | |
|---|---|---|
| | 70° C. | 75° C. |
| KT3-11 | 1.0 | 1.0 |
| D25N | 0.1 | — |
| M57L | 11 | — |
| A62V | 8.3 | — |
| S94P | 2.3 | — |
| E117G | 0.1 | — |
| S190L | 0.1 | — |
| S203P | 1.9 | — |
| D206V + H207Q | 2.5 | — |

TABLE 2-continued

Relative Residual Activity of KT3-11 Mutant Strains

| KT3-11 Mutant Strain | Relative Residual Activity 70° C. | 75° C. |
|---|---|---|
| S220P | 1.3 | — |
| I234V | 2.2 | — |
| T238A | 5.5 | — |
| A62V + S94P | 32 | 1.9 |
| A62V + S94P + M57L + T238A | — | 14 |
| A62V + S94P + M57L + T238A + D206V + H207Q + S220P + I234A | — | 93 |
| A62V + S94P + M57L + T238A + D206V + H207Q + S220P + I234A + S203P | — | 113 |

(Values indicate the relative residual activity after heat treatment for 10 minutes at 70° C. or 75° C., of a lysate of E. coli BL21 (pLysS) strain expressing these mutants)

On the other hand, the three mutations unique to KT3-3; Asp25Asn, Glu117Gly and Ser190Leu operate to destabilize the protein at least in connection with the sequence of KT3-11 (Table 2). "Highly thermostable kanamycin nucleotidyltransferase", HTK, SEQ ID NO: 3 was made by incorporating all nine positive mutations into KT3-11 with an Amersham kit (Sculpters) (Table 1). HTK has 19 amino acid substitutions when compared to WT*. In the preparation of HTK, it was observed that the effect of these mutations on thermostability was essentially additional (See Table 2). The Kcat and Km values of HTK against ATP (in the presence of 2 mM kanamycin) were approximately twice that of WT*, however there was almost no change in the properties of HTK as a catalyst due to the mutations.

TABLE 3

Dynamic parameters of KNT mutant

| | ATP = 5.4 mM | | Kan = 2.0 mM | |
|---|---|---|---|---|
| Enzyme | Km, kan (mM) | Kcat (min − 1) | Km, ATP (mM) | Kcat (min − 1) |
| WT* | 0.46 ± 0.31 | 13 ± 2.6 | 2.7 ± 0.52 | 12 ± 1.1 |
| HTK | 0.59 ± 0.21 | 18 ± 2.3 | 5.9 ± 2.6 | 24 ± 6.7 |

Enzyme activity was measured at 25° C., pH 6.0. Dynamic parameters for one substrate is determined while keeping concentration of the other substrate constant.

kan: kanamycin

Example 4

The Thermostability of Three Types of KNT

Figure 2:
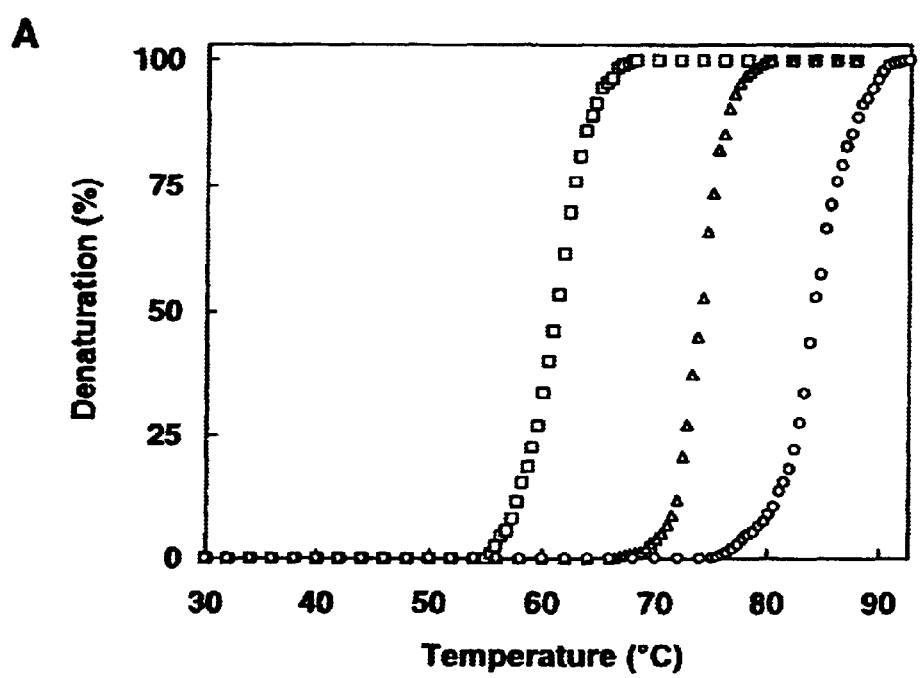
FIG. 2 indicates the thermostability of KNT.

To evaluate the thermostability of WT*, KT3-11, and HTK, the denaturation of each protein was tracked using CD spectroscopy (FIG. 2A). The apparent Tm values of WT*, KT3-11 and HTK were 61, 73 and 84° C., respectively. The denaturation of KNT is irreversible, and KT3-11 and HTK aggregate after denaturation, thus the denaturation curve of FIG. 2A cannot be used in the calculation of value of ΔΔG. To confirm the relative stability of the three types of KNT, after heat treatment for 10 minutes at 60, 72, and 80° C., the residual activity of each KNT was measured (FIG. 2B). At 60° C., the activity of WT* fell to 5%, but there was no change for KT3-11 and HTK. At 72° C., WT* was completely inactivated, the activity of K3-11 fell to 5% and HTK was still active. HTK, even after ten minutes of heat treatment at 80° C., still maintained 15% activity. This result matched well the Tm value obtained from the denaturation curve. It can be said that the thermostability of HTK represents an increase of at least 20° C. when compared that of WT*. WT* possesses two mutations, as described above, and has increased thermostability of about 10° C. compared to that of the wild type KNT. Therefore, the thermostability of HTK was a total of 30° C. higher via the introduction of 21 substitutions than the wild type enzyme of *Staphylococcus aureus*. To the extent of the inventor's knowledge, among projects to improve the thermostability of a protein, this invention can be said to be one of the most successful examples. The thermostabilities of glucose-dehydrogenase and iso-1-cytochrome have been improved by 20° C. and 17° C. respectively (Makino, Y., J. Biol. Chem. 264, 6381–6385 (1989); Nagao, T., FEBS Lett. 253, 113–116 (1989); Das, G., Proc. Natl. Acad. Sci. USA 86, 496–499 (1989)), however each case was as a result of a single amino acid substitution. These two examples are extremely interesting, but our KNT approach is more common. The natural evolution of a protein is thought to proceed through the accumulation of many mutations, and, each mutation makes a small contribution to the overall effect. The concept that the accumulation of small effects is important is supported by the fact that many studies using introduction of a small number of rationally-designed substitutions, end with very limited success. What should be made clear is that the two independent studies to isolate heat resistant KNT mutant strains through a single random mutation and screening, merely found only the same two stable mutants.

Example 5

The Distribution of Modified Residues in the Structure of KNT

With the exception of Val1175 and Ile234 found in the hydrophobic core, all of the other mutations in HTK are found on the surface of the molecule (FIG. 3). At the subunit boundary, there are no mutations. The Gln91Arg substitution probably stabilizes the helical dipole. There are reports of the thermostability of protein being increased with substitutions by proline. In HTK, there are 5 proline substitutions. Ser94 and Ser112 are found on the $2^{nd}$ site of the β-turn, Ser199 and Ser203 on the loop of the surface, and Ser220 on the N-terminal cap structure of the α-helix. Surprisingly, despite the fact that the hydroxyl group of the Ser94 side chain is within hydrogen bonding distance of the 1-amide group of kanamycin, the catalytic efficiency of HTK is almost unchanged with the Ser94Pro mutation.

Example 6

Construction of Convenient Vectors for T. thermophilus

A plasmid incorporating the replication origin of *T. thermophilus,* and the HTK gene, pJHK3 (Restriction map is shown in FIG. 4) is a convenient vector for performing molecular biological experiment with *T. thermophilus*. When pJHK3 is used, it is possible to perform the standard procedures from transformation and singling out colonies to liquid culture, in 2 days. However, with the same protocol using the convention WT*gene, 4 days are required. With the new selective marker of the present invention, research on *T. thermophilus, Thermus aquaticus, Bacillus stearothermophilus* and other such thermophilic bacteria can be greatly accelerated.

As described in detail above, the present invention provides a novel kanamycin nucleotidyltransferase with markedly improved thermostability, a selective marker employing the same, and method for screening thermophilic bacteria such as *Thermus thermophilus* using said selective marker.

With the new selective marker of the present invention, research on *T. thermophilus, Thermus aquaticus, Bacillus stearothermophilus* and other such thermophilic bacteria can be greatly accelerated.

What is claimed is:

1. An isolated mutant kanamycin nucleotidyltransferase comprising the sequence of SEQ ID NO:1 modified by a mutation selected from the group consisting of:

Met57Leu, Ala62Val, Ser94Pro, Ser203Pro, Asp206Val, His207Gln, Ser220Pro, Ile234Val, Thr238Ala, and combinations thereof;

wherein said nucleotidyltansferase has improved thermostability as compared to SEQ ID NO:1.

2. An isolated mutant kanamycin nucleotidyltransferase with improved thermostability as compared to SEQ ID NO:1, comprising the amino acid sequence set forth in SEQ ID NO:2.

3. An isolated mutant kanamycin nucleotidyltransferase comprising the amino acid sequence set forth in SEQ ID NO:3.

4. An isolated mutant kanamycin nucleotidyltransferase comprising the amino acid sequence set forth in SEQ ID NO:12.

5. An isolated mutant kanamycin nucleotidyltransferase comprising the amino acid sequence set forth in SEQ ID NO:13.

6. An isolated mutant kanamycin nucleotidyltransferase comprising the amino acid sequence set forth in SEQ ID NO:14.

7. An isolated mutant kanamycin nucleotidyltransferase comprising the amino acid sequence set forth in SEQ ID NO:15.

8. An isolated mutant kanamycin nucleotidyltrnsferase comprising the amino acid sequence set forth in SEQ ID NO:16.

9. An isolated mutant kanamycin nucleotidyltransferase comprising the amino acid sequence set forth in SEQ ID NO:17.

10. An isolated mutant kanamycin nucleotidyltransferase comprising the amino acid sequence set forth in SEQ ID NO:18.

11. An isolated mutant kanamycin nucleotidyltansferase comprising the amino acid sequence set forth in SEQ ID NO:19.

12. An isolated mutant kanamycin nucleotidyltransferase comprising the amino acid sequence set forth in SEQ ID NO:20.

\* \* \* \* \*

UNITED STATES PATENT AND TRADEMARK OFFICE
CERTIFICATE OF CORRECTION

PATENT NO. : 6,723,543 B1
APPLICATION NO. : 09/697186
DATED : April 20, 2004
INVENTOR(S) : Sigeyuki Yokoyama et al.

It is certified that error appears in the above-identified patent and that said Letters Patent is hereby corrected as shown below:

Claim 8, col. 36, line 17 change "nucleotidyltrnsferase" to --nucleotidyltransferase--.

Signed and Sealed this

Sixth Day of February, 2007

JON W. DUDAS
*Director of the United States Patent and Trademark Office*